(12) United States Patent
Simpson et al.

(10) Patent No.: US 9,006,413 B2
(45) Date of Patent: Apr. 14, 2015

(54) PCP2 MINI-PROMOTERS

(71) Applicant: The University of British Columbia, Vancouver (CA)

(72) Inventors: Elizabeth M. Simpson, Vancouver (CA); Wyeth W. Wasserman, Vancouver (CA); Robert A. Holt, North Vancouver (CA); Steven J. Jones, Vancouver (CA); Daniel Goldowitz, Port Moody (CA); Elodie Portales-Casamar, Vancouver (CA); Cletus D'Souza, Vancouver (CA); Vikramjit Chopra, Vancouver (CA); Charles de Leeuw, Vancouver (CA)

(73) Assignee: The University of British Columbia, Vancouver, B.C. (CA)

( * ) Notice: Subject to any disclaimer, the term of this patent is extended or adjusted under 35 U.S.C. 154(b) by 0 days.

(21) Appl. No.: 14/086,817

(22) Filed: Nov. 21, 2013

(65) Prior Publication Data

US 2014/0141517 A1 May 22, 2014

Related U.S. Application Data

(60) Provisional application No. 61/729,232, filed on Nov. 21, 2012.

(51) Int. Cl.
| | |
|---|---|
| *C07H 21/04* | (2006.01) |
| *C12N 15/63* | (2006.01) |
| *C12N 15/79* | (2006.01) |
| *C12N 15/90* | (2006.01) |
| *C12N 5/07* | (2010.01) |
| *C12N 5/079* | (2010.01) |
| *C12N 15/85* | (2006.01) |

(52) U.S. Cl.
CPC .......... *C12N 15/85* (2013.01); *C12N 2830/007* (2013.01); *C12N 2830/85* (2013.01)

(58) Field of Classification Search
CPC .......... C12N 15/11; C12N 15/63; C12N 5/10; C12N 2830/008; C12N 2830/00; C12N 15/111
USPC ................................ 536/24.1; 435/320.1, 325
See application file for complete search history.

(56) References Cited

PUBLICATIONS

Alam et al. (2002), Gene vol. 282:103-111.*
Muller et al. (1996) J. Mol. Biol. vol. 257:21-29.*
Xie et al. (1992) Molecular and Cellular Biology, vol. 12:1266-1275.*
Attwood (2000) Science, 290:471-473.*
Kyrpides et al. (1999) Mol. Microbiology 32:886-887.*
Gerhold et al. (1996) BioEssays 18:973-981.*
Barski et al. "Cre recombinase expression in cerebellar Purkinje cells" Genesis, (Nov.-Dec. 2000), 28(3-4):93-98.
Hanno et al. "Tracking mouse visual pathways with WGA transgene" Eur J Neurisci, (Nov. 2003), 18(10):2910-2914.
Oberdick et al. "A promoter that drives transgene expression in cerebellar Purkinje and retinal bipolar neurons", Science, (Apr. 1990), 248(4952):223-226.
Serinagaoglu et al. "A promoter element with enhancer properties, and the orphan nuclear receptor RORalpha, are required for Purkinje cell-specific expression of a Gi/o modulator.", Mol Cell Neurosci, (Mar. 2007) 34(3):324-342.
Smeyne et al. "Local control of granule cell generation by cerebellar Purkinje cells", Mol Cell Neurosci, (Jun. 1995), 6 (3):230-251.
Tomomura et al. "Purification of Purkinje cells by fluorescence-activated cell sorting from transgenic mice that express green fluorescent protein", Eur J Neurisci, (Jul. 2001), 14(1):57-63.
Vandaele et al. "Purkinje cell protein-2 regulatory regions and transgene expression in cerebellar compartments", Genes Dev, (Jul. 1991), 5(7):1136-1148.
Yoshihara et al. "A genetic approach to visualization of multisynaptic neural pathways using plant lectin transgene", Neuron, (Jan. 1999), 22(1):33-41.
Zhang et al. "Transgenic mice expressing Cre-recombinase specifically in retinal rod bipolar neurons", Invest Ophthalmol Vic Sci, (Oct. 2005), 46(10):3515-3520.

* cited by examiner

*Primary Examiner* — Anne Marie S Wehbe
(74) *Attorney, Agent, or Firm* — Bozicevic, Field & Francis LLP; Pamela J. Sherwood

(57) ABSTRACT

Isolated polynucleotides comprising a PCP2 mini-promoter are provided. The mini-promoter may be operably linked to an expressible sequence, e.g. reporter genes, genes encoding a polypeptide of interest, regulatory RNA sequences such as miRNA, siRNA, anti-sense RNA, etc., and the like. In some embodiments a cell comprising a stable integrant of an expression vector is provided, which may be integrated in the genome of the cell. The promoter may also be provided in a vector, for example in combination with an expressible sequence. The polynucleotides find use in a method of expressing a sequence of interest, e.g. for identifying or labeling cells, monitoring or tracking the expression of cells, gene therapy, etc.

8 Claims, 3 Drawing Sheets

A

B

C

D

PCP2 MINI-PROMOTERS

FIELD OF THE INVENTION

The invention relates to gene promoters and regulatory elements. More specifically, the invention relates to novel PCP2 promoter compositions and related methods.

BACKGROUND

There is a need for characterized human PCP2 promoters for gene expression, for instance in human gene therapy applications. It is in particular useful to identify small promoter elements that are sufficient to drive expression in certain cell types, for instance retinal bipolar neurons. Such small promoter elements, or "mini-promoters" are particularly useful in certain applications, for instance they are more amenable to insertion into viral vectors used in gene therapy applications.

PCP2 promoter elements (alternatively referred to as L7) from different species are described in the art, including: Oberdick, Smeyne et al. 1990; Vandaele, Nordquist et al. 1991; Smeyne, Chu et al. 1995; Yoshihara, Mizuno et al. 1999; Barski, Dethleffsen et al. 2000; Tomomura, Rice et al. 2001; Hanno, Nakahira et al. 2003; Zhang, Chen et al. 2005; Serinagaoglu, Zhang et al. 2007.

SUMMARY OF THE INVENTION

The present invention provides novel nucleic acid sequence compositions and methods relating to minimal human PCP2 promoters. The invention is based in part on the surprising discovery that certain minimal PCP2 promoter elements are capable of expressing in specific cell types, for instance in retinal cells.

In one embodiment of the invention, there is provided an isolated nucleic acid fragment comprising a PCP2 mini-promoter, wherein the PCP2 mini-promoter comprises a PCP2 regulatory element operably linked in a non-native conformation to a PCP2 basal promoter. In other embodiments, PCP2 mini-promoter comprises a PCP2 basal promoter. The PCP2 mini-promoter may have a nucleic acid sequence which is substantially similar in sequence and function to SEQ ID NO: 1 or 2. The PCP2 regulatory element may have a nucleic acid sequence which is substantially similar in sequence and function to SEQ ID NO: 3. The PCP2 basal promoter may have a nucleic acid sequence which is substantially similar in sequence and function to SEQ ID NO: 2. The PCP2 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule.

In one embodiment, there is provided an expression vector comprising a PCP2 mini-promoter element, wherein the PCP2 mini-promoter element comprises a PCP2 regulatory element operably linked in a non-native conformation to a PCP2 basal promoter element. In another embodiment, the PCP mini-promoter comprises a PCP2 basal promoter. The PCP2 mini-promoter may have a nucleic acid sequence which is substantially similar in sequence and function to SEQ ID NO: 1 or 2. The PCP2 regulatory element may have a nucleic acid sequence which is substantially similar in sequence and function to SEQ ID NO: 3. The PCP2 basal promoter may have a nucleic acid sequence which is substantially similar in sequence and function to SEQ ID NO: 2. The PCP2 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may further comprise a genomic targeting sequence. The genomic targeting sequence may be HPRT.

In one embodiment, there is provided a method for expressing a gene, protein, RNA interference molecule or the like in a cell, the method comprising introducing into the cell an expression vector comprising a PCP2 mini-promoter element, wherein the PCP2 mini-promoter element comprises a PCP2 regulatory element operably linked in a non-native conformation to a PCP2 basal promoter element. In another embodiment, the PCP2 mini-promoter comprises a PCP2 basal promoter. Cells of interest include, without limitation, cells of the peripheral or central nervous system and progenitors thereof, e.g. embryonic stem cells, neural stem cells, neurons, glial cells, astrocytes, microglial cells, etc; and/or cells in the eye and progenitors thereof, e.g. retinal cells, bipolar cells, etc. The PCP2 mini-promoter may have a nucleic acid sequence which is substantially similar in sequence and function to SEQ ID NO: 1 or 2. The PCP2 regulatory element may have a nucleic acid sequence which is substantially similar in sequence and function to SEQ ID NO: 3. The PCP2 basal promoter may have a nucleic acid sequence which is substantially similar in sequence and function to SEQ ID NO: 2. The PCP2 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expressible sequence may encode an RNA interference molecule. The expression vector may thus further comprise a genomic targeting sequence. The genomic targeting sequence may be HPRT.

In one embodiment of the invention, there is provided a method for identifying or labeling a cell, the method comprising introducing into the cell an expression vector comprising a PCP2 mini-promoter element operably linked to an expressible sequence, wherein the PCP2 mini-promoter element comprises a PCP2 regulatory element operably linked in a non-native conformation to a PCP2 basal promoter element, and wherein the expressible sequence comprises a reporter gene. In other embodiments, the PCP2 mini-promoter comprises a PCP2 basal promoter. The PCP2 mini-promoter element may have a nucleic acid sequence substantially similar in sequence and function to SEQ ID NO: 1 or 2. The PCP2 regulatory element may have a nucleic acid sequence substantially similar in sequence and function to SEQ ID NO: 3. The PCP2 basal promoter element may have a nucleic acid sequence substantially similar in sequence and function to SEQ ID NO: 2. In some embodiments, the cell is a peripheral or central nervous system cell or progenitors thereof, including, without limitation, embryonic stem cells, neural stem cells, glial cells, astrocytes, neurons and the like, and/or cells in the eye and progenitors thereof, e.g. retinal cells, bipolar cells, etc.. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In one embodiment of the invention, there is provided a method for monitoring or tracking the development or maturation of a cell, the method comprising: 1) introducing into the cell an expression vector comprising a PCP2 mini-promoter element operably linked to an expressible sequence, wherein the PCP2 mini-promoter element comprises a PCP2 regulatory element operably linked in a non-native conformation to a PCP2 basal promoter element, and wherein the expressible sequence comprises a reporter gene; and 2) detecting the expression of the reporter gene in the cell of in progeny of the cell as a means of determining the lineage, identity or developmental state of the cell or cell progeny. In other embodiments, the PCP2 mini-promoter comprises a PCP2 basal promoter. The PCP2 mini-promoter element may have a nucleic acid sequence substantially similar in sequence and function to SEQ ID NO: 1 or 2. The PCP2 regulatory element may have a nucleic acid sequence substantially similar in sequence and function to SEQ ID NO: 3. The PCP2 basal promoter element may have a nucleic acid sequence substantially similar in sequence and function to SEQ ID NO: 2. In some embodiments, the cell is a peripheral or central nervous system cell or progenitors thereof, including, without limitation, embryonic stem cells, neural stem cells, glial cells, neurons and the like. In some embodiments, the cell is an eye cell or progenitor thereof, including without limitation a retinal cell, a retinal bipolar cell, and the like.

BRIEF DESCRIPTION OF FIGURES

FIG. 3—Positive expression from the Ple155 construct. A) Ple155-lacZ (PCP2) expression in the adult mouse brain. Adult mouse brain was perfused and stained with X-Gal overnight. Expression of the Ple155-lacZ construct is demonstrated in a subpopulation of cells residing in the anterior thalamus. This is a novel expression pattern representing a specific cell population. Limited expression is also found in some aspects of the hypothalamus. B) Ple155-lacZ (PCP2) expression in the neural retina of mouse eye. Expression is clearly found in the inner nuclear layer of the retina. There are processes or additional staining observed in the inner plexiform layer. The expression pattern is consistent with the known expression of the PCP2 gene in bipolar cells. C) Ple155-lacZ (PCP2) expression is consistent between mice. An additional mouse demonstrates the same expression pattern, but with lighter β-galactosidase staining overall. D) FIG. 3. Ple155-lacZ (PCP2) expression is localized to the inner nuclear layer and innerplexiform layer, consistent with bipolar cells. Layers of the retina are indicated in white text (confirmed with neutral red counterstaining, not shown). The inner nuclear layer is where the predominant staining is observed (also the localization of bipolar cells), with additional strong staining present in the inner plexiform layer, where bipolar cell processes extend to.

DETAILED DESCRIPTION

Figure 1:
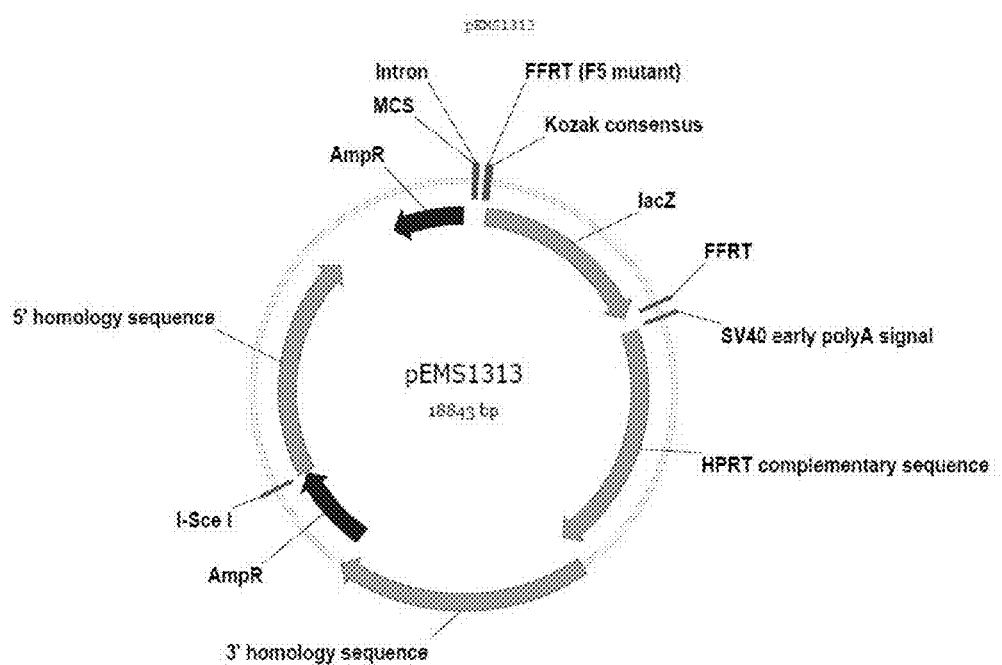
FIG. 1—DNA expression vector (pEMS1313) into which PCP2 promoter elements were inserted for expression studies. The PCP2 promoter with a nucleic acid sequence corresponding to SEQ ID NO: 1 was inserted into the multiple cloning site (MCS) of the pEMS1313 vector such that it became operably linked to the lac Z reporter gene. The final construct, called Ple155 also contained the HPRT genomic targeting sequence, an ampicillin resistance gene (AmpR) for screening, and a transcriptional termination sequence (SV40 polyA), as well as other elements necessary for vector replication and gene expression.

The compositions of the present invention include novel polynucleotides comprising
PCP2 promoter elements (also referred to herein as PCP2 mini-promoters) as well as novel expression vectors comprising said PCP2 promoter elements (or mini-promoters). The present invention also includes various methods utilizing these novel PCP2 promoter (or mini-promoter) elements or expression vectors.

The term 'PCP2' refers to the gene which encodes the PCP2 protein, also referred to as Purkinje cell protein 2, L7 and/or GPSM4. The human homolog of PCP2 is encoded by the human gene identified as EntrezGene # 126006 and is located at chromosomal location 19p13.2. The protein encoded by human PCP2 has the Protein Accession # AAH25387.1, however other protein accession numbers may also be assigned to this protein. PCP2 may also include other isoforms and/or splice variants. Other mammalian PCP2 homologs may include but are not limited to: Rattus norvegicus (EntrezGene # 304195), Mus musculus (EntrezGene #18545, Protein Accession # P12660.2).

The term 'promoter' refers to the regulatory DNA region which controls transcription or expression of a gene and which can be located adjacent to or overlapping a nucleotide or region of nucleotides at which RNA transcription is initiated. A promoter contains specific DNA sequences which bind protein factors, often referred to as transcription factors, which facilitate binding of RNA polymerase to the DNA leading to gene transcription. A 'basal promoter', also referred to as a 'core promoter', usually means a promoter which contains all the basic necessary elements to promote transcriptional expression of an operably linked polynucleotide. Eukaryotic basal promoters typically, though not necessarily, contain a TATA-box and/or a CAAT box. A 'PCP2 basal promoter', in the context of the present invention and as used herein, is a nucleic acid compound having a sequence with at least 65%, at least 70%, at least 80%, at least 85%, at least 90%, at least 95%, or at least 99% similarity to SEQ ID NO: 2.

A promoter may also include 'regulatory elements' that influence the expression or transcription by the promoter. Such regulatory elements encode specific DNA sequences which bind other factors, which may include but are not limited to enhancers, silencers, insulators, and/or boundary elements. A 'PCP2 regulatory element', in the context of the present invention and as used herein, is a nucleic acid compound having a sequence with at least 65%, at least 70%, at least 80%, at least 85%, at least 90%, at least 95%, or at least 99% similarity to SEQ ID NO: 3. The present invention provides, in certain embodiments as described herein, different promoters of the PCP2 gene. In some embodiments, the PCP2 promoter comprises a PCP2 regulatory element operably linked to a PCP2 basal promoter in a non-native configuration, e.g. a nucleic acid compound having a sequence with at least 65%, at least 70%, at least 80%, at least 85%, at least 90%, at least 95%, or at least 99% similarity to SEQ ID NO:1.

The term 'operably linked', in the context of the present invention, means joined in such a fashion as to work together to allow transcription. In some embodiments of the invention, two polynucleotide sequences may be operably linked by being directly linked via a nucleotide bond. In this fashion, the two operably linked elements contain no intervening sequences and in being joined are able to direct transcription of an expression sequence. In other embodiments of the invention, two elements may be operably linked by an intervening compound, for instance a polynucleotide sequence of variable length. In such a fashion, the operably linked elements, although not directly juxtaposed, are still able to direct transcription of an expression sequence. Thus, according to some embodiments of the invention, one or more promoter elements may be operably linked to each other, and additionally be operably linked to a downstream expression sequence, such that the linked promoter elements are able to direct expression of the downstream expression sequence.

The term 'mini-promoter' refers to a promoter in which certain promoter elements are selected from an endogenous full length promoter for a gene, usually in such a fashion as to reduce the overall size of the promoter compared to the native sequence. For example, after identification of critical promoter elements, using one or more of various techniques, the native sequences that intervene between identified elements may be partially or completely removed. Other non-native sequences may optionally be inserted between the identified promoter elements. Promoter sequences such as enhancer elements may have an orientation that is different from the native orientation—for example, a promoter element may be inverted, or reversed, from its native orientation. Alternatively, selecting a minimal basal promoter that is sufficient to drive expression in particular cells or tissues may also be desirable. Since promoter elements that impact expression patterns are known to be distributed over varying distances of the proximal and/or distal endogenous promoter, it is a non-trivial task to identify a mini-promoter comprising a minimal basal promoter and optional regulatory regions that will adequately express in the desired cell or tissue types. A mini-promoter may provide certain advantages over native promoter conformations. For example, the smaller size of the mini-promoter can allow easier genetic manipulation, for example in the design and/or construction of expression vectors or other recombinant DNA constructs. In addition, the smaller size can allow easier insertion of DNA constructs into host cells and/or genomes, for example via transfection, transformation, etc. Other advantages of mini-promoters are apparent to one of skill in the art. In some embodiments of the invention, there are thus provided novel PCP2 mini-promoters comprising a PCP2 regulatory element as defined above, operably linked in a non-native conformation to a PCP2 basal promoter, as defined above. In general the spacing between the PCP2 regulatory element and the PCP2 basal promoter is not more than about 15 KB, generally not more than about 10 KB, usually not more than about 1 KB, more often not more than about 500 nt, and may be not more than about 100 nt, down to a direct joining of the two sequences. In other embodiments, there is provided a minimal PCP2 basal promoter.

The term 'expressible sequence' refers to a polynucleotide composition which is operably linked to a promoter element such that the promoter element is able to cause transcriptional expression of the expression sequence. An expressible sequence is typically linked downstream, on the 3'-end of the promoter element(s) in order to achieve transcriptional expression. The result of this transcriptional expression is the production of an RNA macromolecule. The expressed RNA molecule may encode a protein and may thus be subsequently translated by the appropriate cellular machinery to produce a polypeptide protein molecule. In some embodiments of the invention, the expression sequence may encode a reporter protein. Alternately, the RNA molecule may be an antisense, RNAi or other non-coding RNA molecule, which may be capable of modulating the expression of specific genes in a cell, as is known in the art.

The term 'RNA' as used in the present invention includes full-length RNA molecules, which may be coding or non-coding sequences, fragments, and derivatives thereof. For example, a full-length RNA may initially encompass up to about 20 Kb or more of sequence, and frequently will be processed by splicing to generate a small mature RNA. Fragments, RNAi, miRNA and anti-sense molecules may be smaller, usually at least about 18 nt. in length, at least about 20 nt in length, at least about 25 nt. in length, and may be up to about 50 nt. in length, up to about 100 nt in length, or more. RNA may be single stranded, double stranded, synthetic, isolated, partially isolated, essentially pure or recombinant. RNA compounds may be naturally occurring, or they may be altered such that they differ from naturally occurring RNA compounds. Alterations may include addition, deletion, substitution or modification of existing nucleotides. Such nucleotides may be either naturally occurring, or non-naturally occurring nucleotides. Alterations may also involve addition or insertion of non-nucleotide material, for instance at the end or ends of an existing RNA compound, or at a site that is internal to the RNA (ie. between two or more nucleotides).

The term 'nucleic acid' as used herein includes any nucleic acid, and may be a deoxyribonucleotide or ribonucleotide polymer in either single or double-stranded form. A 'polynucleotide' or 'nucleotide polymer' as used herein may include synthetic or mixed polymers of nucleic acids, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoamidates, carbamates, etc.), charged linkages (e. g., phosphorothioates, phosphorodithioates, etc.), pendent moieties (e.g., polypeptides), and modified linkages (e.g., alpha anomeric polynucleotides, etc.). Also included are synthetic molecules that mimic polynucleotides in their ability to bind to a designated sequence via hydrogen bonding and other chemical interactions.

A 'purine' is a heterocyclic organic compound containing fused pyrimidine and imidazole rings, and acts as the parent compound for purine bases, adenine (A) and guanine (G). 'Nucleotides' are generally a purine (R) or pyrimidine (Y) base covalently linked to a pentose, usually ribose or deoxyribose, where the sugar carries one or more phosphate groups. Nucleic acids are generally a polymer of nucleotides joined by 3' 5' phosphodiester linkages. As used herein 'purine' is used to refer to the purine bases, A and G, and more broadly to include the nucleotide monomers, deoxyadenosine-5'-phosphate and deoxyguanosine-5'-phosphate, as components of a polynucleotide chain. A 'pyrimidine' is a single-ringed, organic base that forms nucleotide bases, such as cytosine (C), thymine (T) and uracil (U). As used herein 'pyrimidine' is used to refer to the pyrimidine bases, C, T and U, and more broadly to include the pyrimidine nucleotide monomers that along with purine nucleotides are the components of a polynucleotide chain.

It is within the capability of one of skill in the art to modify the sequence of a promoter nucleic acid sequence, e.g. the provided basal promoter and regulatory sequences, in a manner that does not substantially change the activity of the promoter element, i.e. the transcription rate of an expressible sequence operably linked to a modified promoter sequence is at least about 65% the transcription rate of the original promoter, at least about 75% the transcription rate of the original promoter sequence, at least about 80%, at least about 90%, at least about 95%, at least about 99%, or more. Such modified sequences would be considered to be 'functionally similar' or to have 'functional similarity' or 'substantial functional similarity' to the unmodified sequence. Such modifications may include insertions, deletions which may be truncation of the sequence or internal deletions, or substitutions. The level of sequence modification to an original sequence will determine the 'sequence similarity' of the original and modified sequences. Modification of the promoter elements of the present invention in a fashion that does not significantly alter transcriptional activity, as described above would result in sequences with 'substantial sequence similarity' to the original sequence i.e. the modified sequence has a nucleic acid composition that is at least about 65% similar to the original promoter sequence, at least about 75% similar to the original promoter sequence, at least about 80%, at least about 90%, at least about 95%, at least about 99%, or more similar to the original promoter sequence. Thus, mini-promoter elements which have substantial functional and/or sequence similarity are herein described and are within the scope of the invention.

An 'RNA interference molecule', or 'RNA interference sequence' as defined herein, may include, but is not limited to, an antisense RNA molecule, a microRNA molecule or a short hairpin RNA (shRNA) molecule. Typically, RNA interference molecules are capable of target-specific modulation of gene expression and exert their effect either by mediating degradation of the mRNA products of the target gene, or by preventing protein translation from the mRNA of the target gene. The overall effect of interference with mRNA function is modulation of expression of the product of a target gene. This modulation can be measured in ways which are routine in the art, for example by Northern blot assay or reverse transcriptase PCR of mRNA expression, Western blot or ELISA assay of protein expression, immunoprecipitation assay of protein expression, etc.

An 'antisense RNA molecule', as used herein, is typically a single stranded RNA compound which binds to complementary RNA compounds, such as target mRNA molecules, and blocks translation from the complementary RNA compounds by sterically interfering with the normal translational machinery. Specific targeting of antisense RNA compounds to inhibit the expression of a desired gene may design the antisense RNA compound to have a homologous, complementary sequence to the desired gene. Perfect homology is not necessary for inhibition of expression. Design of gene specific antisense RNA compounds, including nucleotide sequence selection and additionally appropriate alterations, are known to one of skill in the art.

The term ThicroRNA molecule', ThicroRNA' or 'miRNA', as used herein, refers to single-stranded RNA molecules, typically of about 21-23 nucleotides in length, which are capable of modulating gene expression. Mature miRNA molecules are partially complementary to one or more messenger RNA (mRNA) molecules, and their main function is to downregulate gene expression. Without being bound by theory, miRNAs are first transcribed as primary transcripts or pri-miRNA with a cap and poly-A tail and processed to short, 70-nucleotide stem-loop structures known as pre-miRNA in the cell nucleus. This processing is performed in animals by a protein complex known as the Microprocessor complex, consisting of the nuclease Drosha and the double-stranded RNA binding protein Pasha. These pre-miRNAs are then processed to mature miRNAs in the cytoplasm by interaction with the endonuclease Dicer, which also initiates the formation of the RNA-induced silencing complex (RISC). When Dicer cleaves the pre-miRNA stem-loop, two complementary short RNA molecules are formed, but only one is integrated into the RISC complex. This strand is known as the guide strand and is selected by the argonaute protein, the catalytically active RNase in the RISC complex, on the basis of the stability of the 5' end. The remaining strand, known as the anti-guide or passenger strand, is degraded as a RISC complex substrate. After integration into the active RISC complex, miRNAs base pair with their complementary mRNA molecules and induce mRNA degradation by argonaute proteins, the catalytically active members of the RISC complex. Animal miRNAs are usually complementary to a site in the 3' UTR whereas plant miRNAs are usually complementary to coding regions of mRNAs.

The term 'short hairpin RNA' or 'shRNA' refers to RNA molecules having an RNA sequence that makes a tight hairpin turn that can be used to silence gene expression via RNA interference. The shRNA hairpin structure is cleaved by the cellular machinery into siRNA, which is then bound to the RNA-induced silencing complex (RISC). This complex binds to and cleaves mRNAs which match the siRNA that is bound to it. shRNA is transcribed by RNA Polymerase III whereas miRNA is transcribed by RNA Polymerase II. Techniques for designing target specific shRNA molecules are known in the art.

An 'expression vector' is typically a nucleic acid molecule which may be integrating or autonomous, (i.e. self-replicating), and which contains the necessary components to achieve transcription of an expressible sequence in a target cell, when introduced into the target cell. Expression vectors may include plasmids, cosmids, phage, YAC, BAC, mini-chromosomes, viruses, e.g. retroviruses, adenovirus, lentivirus, SV-40, and the like; etc. Many such vectors have been described in the art and are suitable for use with the promoters of the present invention. Expression vectors of the present invention include a promoter as described herein, operably linked to an expressible sequence, which may also be optionally operably linked to a transcription termination sequence, such as a polyadenylation sequence. The expression vector optionally contains nucleic acid elements which confer host selectivity, elements that facilitate replication of the vector, elements that facilitate integration of the vector into the genome of the target cell, elements which confer properties, for example antibiotic resistance, to the target cell which allow selection or screening of transformed cells and the like. Techniques and methods for design and construction of expression vectors are well known in the art.

It may be desirable, when driving expression of an expressible sequence with a particular promoter system to have the expression occur in a stable and consistent manner. A factor that has been shown to affect expression is the site of integration of an expression vector or construct into the genome of the target cell, sometimes called 'position effects'. Such position effects may be caused by, for example, local chromatin structure which affects expression of sequences from that region of the genome. One method to control for position effects when integrating an expression vector or construct into the genome of a target cell is to include a 'genomic targeting sequence' in the vector or construct that directs integration of the vector or construct to a specific genomic site. As an example, the hypoxanthine phosphoribosyltransferase (HPRT) gene has been used successfully for this purpose (Bronson, Plaehn et al. 1996; Jasin, Moynahan et al. 1996). The HPRT gene has additional advantages as a genomic targeting sequence, for instance its concomitant use as a selectable marker system. Other genomic targeting sequences that may be useful in the present invention are described in the art, for instance (Jasin, Moynahan et al. 1996; van der Weyden, Adams et al. 2002). The genomic targeting signals as described herein are useful in certain embodiments of the present invention.

Introduction of nucleic acids or expression vectors may be accomplished using techniques well known in the art, for example microinjection, electroporation, particle bombardment, or chemical transformation, such as calcium-mediated transformation, as described for example in Maniatis et al. 1982, Molecular Cloning, A laboratory Manual, Cold Spring Harbor Laboratory or in Ausubel et al. 1994, Current protocols in molecular biology, John Wiley and Sons.

PCP2 Mini-Promoters

The present invention herein provides novel PCP2 mini-promoter sequences which are capable of effecting transcriptional expression in a spatial and temporal fashion in the brain and/or eye. Certain PCP2 mini-promoters of the invention comprise minimal PCP2 promoter elements joined in a non-native configuration, thus providing advantageous characteristics. Other PCP2 mini-promoters of the invention comprise a minimal PCP2 basal promoter. Also provided are novel expression vector compositions comprising PCP2 mini-promoters which allow consistent specific spatiotemporal transcription of expression sequences. Also provided are novel methods utilizing these PCP2 mini-promoters and expression vectors.

The PCP2 promoters of the invention, as described herein, are referred to as 'mini-promoters' to reflect the fact that the mini-promoters comprise minimal PCP2 promoter elements sufficient to drive expression, and that may also be joined by non-native sequences. In this context, the native intervening sequences may have been partially or completely removed, and optionally may have been replaced with non-native sequences. Furthermore, the natural spatial arrangement of elements may be altered, such that downstream promoter elements (in natural conformation) are moved upstream (in non-native conformation). In such a fashion, the natural spacing of the promoter elements, for instance the human PCP2 regulatory element corresponding to SEQ ID NO: 3 and the human PCP2 basal promoter element corresponding to SEQ ID NO: 2, or sequences with substantial functional and/or sequence equivalence, is altered. Additionally, the orientation of the different promoter elements may be altered—for instance the regulatory element corresponding to SEQ ID NO: 3 may be inverted relative to the basal promoter element corresponding to SEQ ID NO: 2. An advantage of such non-native mini-promoters is that the removal of native intervening sequences reduces the size of the mini-promoter while maintaining the functional activity of the promoter, thus improving the utility of the mini-promoter for various applications. Furthermore, the inversion of an enhancer/promoter element may allow retention of the enhancer properties without causing alternate promoter activity.

The inventors have demonstrated, as illustrated in the non-limiting Working Examples, that a human PCP2 mini-promoter having a sequence corresponding to SEQ ID NO: 1 (also referred to in the Working Examples as Ple155), and which is comprised of a human PCP2 regulatory element having a nucleic acid sequence corresponding to SEQ ID NO: 3 operably linked in a non-native conformation to a human PCP2 basal promoter having a nucleic acid sequence corresponding to SEQ ID NO: 2, is capable of directing expression of an expressible sequence which is operably linked downstream of the PCP2 promoter in specific cell types in different regions of the brain and/or eye. The PCP2 regulatory element (SEQ ID NO: 3) and PCP2 basal promoter element (SEQ ID NO: 2) have sequences which are identical to those found in the human PCP2 gene. It is within the skill of one in the art to locate and determine these relative positions based on published sequence information for this gene, for instance found in the GenBank or PubMed public databases. It is understood that these genomic coordinates and relative positions are provided for the purposes of context, and that if any discrepancies exist between published sequences and the sequence listings provided herein, then the sequence listings shall prevail.

Promoters of the present invention may be modified with respect to the native regulatory and/or native basal promoter sequence. In general, such modifications will not change the functional activity of the promoter with respect to cell-type selectivity; and to the rate of transcription in cells where the promoter is active. The modified promoter provide for a transcription rate of an expressible sequence operably linked to a modified promoter sequence that is at least about 75% the transcription rate of the promoter sequence of SEQ ID NO:1 or 2, at least about 80%, at least about 90%, at least about 95%, at least about 99%, or more. Methods of assessing promoter strength and selectivity are known in the art, including, for example, expression of a reporter sequence in a cell in vivo or in vitro, and quantitating the reporter activity.

Modifications of interest include deletion of terminal or internal regions, and substitution or insertion of residues. The spacing of conserved sequences may be the same as the native spacing, or it may be different than the native spacing. The order of the conserved sequences may be the same as the native order or the sequences may be rearranged. Sequences set forth in SEQ ID NO: 1 or 2 that are not conserved may be deleted or substituted, usually modifications that retain the spacing between conserved sequences is preferred. In general the spacing between the regulatory element and the basal promoter is not more than about 10 KB, generally not more than about 1 KB, usually not more than about 500 nt, and may be not more than about 100 nt, down to a direct joining of the two sequences.

In some embodiments of the invention, there is thus provided an isolated nucleic acid fragment comprising a PCP2 mini-promoter, wherein the PCP2 mini-promoter comprises a PCP2 regulatory element operably linked in a non-native conformation to a PCP2 basal promoter. In other embodiments, the PCP2 mini-promoter comprises a PCP2 basal promoter. In certain embodiments of the invention, the PCP2 promoter may have a nucleic acid sequence which is substantially similar in sequence and function to SEQ ID NO: 1 or 2. In some embodiments, the PCP2 regulatory element may have a nucleic acid sequence which is substantially similar in sequence and function to SEQ ID NO: 3. In some embodiments, the PCP2 basal promoter may have a nucleic acid sequence which is substantially similar in sequence and function to SEQ ID NO: 2. The PCP2 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like.

It is an object of the present invention to provide means of expressing a gene, protein, RNA interference molecule or the like in a cell, tissue or organ. As such, the inventors thus provide novel expression vectors comprising PCP2 mini-promoters which are capable of accomplishing this task. In some embodiments of the invention, there is provided an expression vector comprising a PCP2 promoter element, wherein the PCP2 promoter element comprises a PCP2 regulatory element operably linked in a non-native conformation to a PCP2 basal promoter element. In other embodiments, the PCP2 mini-promoter comprises a PCP2 basal promoter. The PCP2 mini-promoter element may have a nucleic acid sequence substantially similar in sequence and function to SEQ ID NO: 1 or 2. The PCP2 regulatory element may have a nucleic acid sequence substantially similar in sequence and function to SEQ ID NO: 3. The PCP2 basal promoter element may have a nucleic acid sequence substantially similar in sequence and function to SEQ ID NO: 2. The PCP2 mini-promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may further comprise a genomic targeting sequence. The genomic targeting sequence may be HPRT, e.g. human HPRT, mouse HPRT, etc.

The inventors have herein demonstrated that expression vectors comprising novel PCP2 mini-promoter elements are capable of directing transcription of an expression sequence in specific cell types, for instance in bipolar cells in the retina (eye). In some embodiments of the invention, there is thus provided a method for expressing a gene, protein, RNA interference molecule or the like in targeted cells. Cells of interest include, without limitation, cells of the peripheral or central nervous system and progenitors thereof, e.g. embryonic stem cells, neural stem cells, neurons, glial cells, astrocytes, microglial cells, etc; cells of the eye and progenitors thereof, e.g. retinal cells, bipolar cells, etc. The method comprises introducing into a cell or progenitor cell thereof an expression vector comprising a PCP2 mini-promoter element, wherein the PCP2 mini-promoter element comprises a PCP2 regulatory element operably linked in a non-native conformation to a PCP2 basal promoter element. In some embodiments, the PCP2 mini-promoter comprises a PCP2 basal promoter. The PCP2 promoter element may have a nucleic acid sequence substantially similar in sequence and function to SEQ ID NO: 1 or 2. The PCP2 regulatory element may have a nucleic acid sequence substantially similar in sequence and function to SEQ ID NO: 3. The PCP2 basal promoter element may have a nucleic acid sequence substantially similar in sequence and function to SEQ ID NO: 2. The PCP2 promoter may further be operably linked to an expressible sequence, e.g. reporter genes, genes encoding a polypeptide of interest, regulatory RNA sequences such as miRNA, siRNA, anti-sense RNA, etc., and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, and the like. The expression vector may thus further comprise a genomic targeting sequence. The genomic targeting sequence may be HPRT.

In other embodiments of the invention, there is provided a method for identifying or labeling a cell, the method comprising introducing into the cell a expression vector comprising a PCP2 mini-promoter element operably linked to an expressible sequence, wherein the PCP2 mini-promoter element comprises a PCP2 regulatory element operably linked in a non-native conformation to a PCP2 basal promoter element, and wherein the expressible sequence comprises a reporter gene. In some embodiments, the PCP2 mini-promoter comprises a PCP2 basal promoter. The PCP2 promoter element may have a nucleic acid sequence substantially similar in sequence and function to SEQ ID NO: 1 or 2. The PCP2 regulatory element may have a nucleic acid sequence substantially similar in sequence and function to SEQ ID NO: 3. The PCP2 basal promoter element may have a nucleic acid sequence substantially similar in sequence and function to SEQ ID NO: 2. The inventors have demonstrated that expression vectors comprising certain human PCP2 promoter elements are capable of expression in specific regions of the brain and eye, most notably retinal bipolar cells in the eye. In some embodiments, the cell is a peripheral or central nervous system cell or progenitors thereof, including, without limitation, embryonic stem cells, neural stem cells, glial cell, neuronal cells, astrocytes, and the like. In some embodiments, the cell is a cell of the eye and progenitors thereof, including without limitation retinal cells, retinal bipolar cells, and the like. Reporter gene sequences include, for example luciferase, beta-galactosidase, green fluorescent protein, enhanced green fluorescent protein, and the like as known in the art. The expressible sequence may encode a protein of interest, for example a therapeutic protein, receptor, antibody, growth factor, RNA interference molecule and the like.

In further embodiments of the invention, there is provided a method for monitoring or tracking the development or maturation of a brain cell or a retinal cell. The method comprises: 1) introducing into a progenitor to a brain cell or a retinal cell, e.g. an embryonic stem cells, or other progenitor cell, an expression vector comprising a PCP2 mini-promoter element operably linked to an expressible sequence, wherein the PCP2 mini-promoter element comprises a PCP2 regulatory element operably linked in a non-native conformation to a PCP2 basal promoter element, and wherein the expressible sequence comprises a reporter gene; and 2) detecting the expression of the reporter gene in brain or retinal cell progeny of the progenitor cells as a means of determining the lineage, identity or developmental state of the progenitor cell or progeny thereof. In some embodiments, the PCP2 mini-promoter is a PCP2 basal promoter. In such a fashion, one may be able to follow the development of a parent cell as it differentiates into more mature cells. As an example, one could introduce an expression vector comprising the aforementioned PCP2 mini-promoter elements into a pluripotent stem cell, monitor the expression of the reporter gene that is being expressed by the PCP2 promoter elements during the maturation and differentiation of the stem cell and thus determine the state of maturation, for instance in the differentiation of the pluripotent stem cell into a specific brain or retinal cell type. The inventors have demonstrated that the PCP2 mini-promoter elements described herein direct transcriptional expression in certain brain and retinal cell types, and so detection of reporter gene expression in a cell would thus be indicative of the cellular identity of the cell as being a certain type of brain or retinal cell.

The inventors herein further describe the present invention by way of the following non-limiting examples:

EXAMPLES

General Methods

Expression vector. The nucleic acid fragment corresponding to SEQ ID NO: 1 was inserted into the multiple cloning site of pEMS1313 (driving the lacZ reporter, see FIG. 1) to produce the expression vectors (called Ple155) used in the experiments. This resulted in pEMS1626 for Ple155.

Derivation of mEMS1202 embryonic stem cells. Blastocysts were obtained from natural mating of B6-Hprtb-m3 homozygous females to 129-ROSA26 heterozygous males at 3.5 dpc. Blastocysts were flushed from uterine horns as per (Hogan, Beddington et al. 1994), cultured in EmbryoMax® KSOM with 1/2 Amino Acids, Glucose and Phenol Red (Cat # MR-121, Millipore/Chermicon, Temecula, Calif.) for 3-5 h, and then transferred onto mitomycin C (mitC; Cat#M4287, Sigma, Oakville, ON) mitotically inactivated B6-Hprtb-m3, B6129F1, or 129 mouse embryonic feeders (MEFs) derived from 13.5-day post-coital embryos (Ponchio, Duma et al. 2000) in 96-well plates containing KSR-ESC (Knockout™ D-MEM, Cat#10829-018, Invitrogen, Burlington, ON) with 2 mM L-glutamine (Cat#25030-081, Invitrogen, Burlington, ON), 0.1 mM MEM nonessential amino acid solution (Cat#11140-050, Invitrogen, Burlington, ON) and 16% Knockout™ Serum Replacement (Cat#10828-028, Invitrogen, Burlington, ON)) media (MEF media was replaced 3-5 hour prior to transfer).

Blastocysts were cultured as per (Cheng, Dutra et al. 2004) with the following modifications: Cells were cultured for 7-9 days in KSR-ESC with minimal disturbance (checked on day 2 to determine if the blastocysts had 'hatched' out of the zona pellucida) and no media changes. Blastocysts which hatched and had a well-developed ICM (inner cell mass) were treated with 20 µl 0.25% trypsin-EDTA (Invitrogen, Burlington, ON) for 5 min at 37° C., triturated with a 200 µl Pipetman, inactivated with 30 µl 0.5 mg/ml soybean trypsin inhibitor (Invitrogen, Burlington, ON), and brought up to 200 µl with KSR-ESC, then transferred individually to a 24-well MEF plate containing 1800 µl KSR-ESC, for a total volume of 2 ml. Beginning 4 days later, KSR-ESC media was replaced with FBS-ESC media (DMEM (Cat #11960-069, Invitrogen, Burlington, ON) with 2 mM L-glutamine (Invitrogen, Burlington, ON), 0.1 mM MEM nonessential amino acid solution (Invitrogen, Burlington, ON), 16% ES Cell Qualified fetal bovine serum (FBS, Invitrogen, Burlington, ON), 1000 U ESGRO-LIF (Millipore, ESG1107) and 0.01% β-mercaptoethanol (Sigma, Oakville, ON)) in 25%, 50%, 75% proportions (respectively) to adapt the cells to FBS-containing media.

On day 7 the cells were trypsinized to one well of a 24 well plate containing 1 ml of 100% FBS-ESC media, with daily media replacement. Once confluent, wells containing ESC colonies were expanded 3×24 wells (with MEFs), then passaged to 3×24 (with MEFs) and 3×12 well (plastic—no MEFs) for DNA analysis. Once confluent, the 3×24 wells were combined, aliquoted (3 vials), and frozen in ESC-freeze media (50% FBS, 40% FBS-ESC media, 10% DMSO (Sigma, Oakville, ON), and the 3×12 well treated with lysis buffer (Fisher Scientific, Ottawa, ON), mixed and aliquoted. Cultures were genotyped for X & Y chromosomes (Clapcote and Roder 2005), Gt(ROSA)26Sortm1Sor and WT alleles and Hprtb-m3 and WT alleles. B6129F1-Gt(ROSA) 26Sortm1Sor/+, Hprtb-m3/Y (mEMS1204 series) and B6129F1-Gt(ROSA)26Sortm1Sor+/+, Hprtb-m3/Y (mEMS1202 series) cell lines were identified.

Knock-in at the Hprt locus. The Ple155 expression vector plasmid DNA was purified with Qiagen Maxi Kit (Qiagen, Mississauga, ON), resuspended in 10:1 Tris-EDTA (TE, pH7.0) buffer, and linearized with I-ScI (New England Biolabs, Pickering, ON). Linearized plasmid DNA was resuspended in 85 µl of TE (10:0.1) to a final concentration of 187.5 ng/µl . Ple155 was targeted in our in-house derived mEMS1202 cell line. ESCs were grown to confluence on 4-6 T75 flasks of mitC treated Hprtb-m3 mouse embryonic feeders (MEFs) in FBS-ESC media. ESCs (1.7-2.5×107) in 720 µl 1× PBS were added to the linearized DNA and electroporated in a 4 mm electroporation cuvette (Bio-Rad Genepulser, Mississauga, ON), at 240 V, 50 µF, 6-10 msec pulse, immediately resuspended in a total volume of 5 ml of FBS-ESC media and plated onto 5×100 mm dishes of mitC B6129F1 MEFs in a total volume of 12 ml per 100 mm dish.

24-36 h post-electroporation, correctly targeted homologous recombinants were selected for using HAT media (FBS-ESC media containing 1×HAT ((0.1 mM sodium hypoxanthine, 0.4 mM aminopterin, 0.16 mM thymidine), Cat#21060-017, Invitrogen, Burlington, ON). HAT media was changed every day for the first 3 days, and then every 3rd day thereafter, for up to 10 days. Individual colonies were counted and, typically, no more than 2 isolated colonies were picked per 100 mm dish to optimize for independent homologous recombination events. These colonies were expanded under standard protocols for verification of the desired recombination event.

Derivation of knock-in mice. Chimeric mice from targeted ESCs were generated by microinjection (Hogan, Beddington et al. 1994) into E3.5 blastocysts followed by implantation into the uterine horns of 2.5 day pseudopregnant ICR females. Chimeras were identified and coat color chimerism determined as outlined below.

Male chimeras derived from the E14TG2a cell lines were mated with B6 or B6-Alb females, and germline transmission was identified in the former case by the transmission of the dominant Aw (white bellied agouti) allele, making the progeny appear brown with a cream belly, or in the latter case by the combination of Aw and Tyrc-ch (chinchilla), making the progeny appear golden. Non-germline progeny from the cross to B6 were homozygous for the recessive a (nonagouti) allele and appeared black, whereas non-germline progeny from the cross to B6-Alb were homozygous for the recessive Tyrc-2J (albino 2 Jackson) allele and appeared white.

Male chimeras derived from the mEMS1202 cell lines were mated with B6-Alb females, and germline transmission identified by the presence of the dominant Tyr+ (tyrosinase; wild type) and the Aw (white bellied agouti) or a (nonagouti) alleles making the progeny appear brown with a cream belly or black, respectively. Non-germline progeny were homozygous for the recessive Tyrc-2J (albino 2 Jackson) allele and appeared white. All germline female offspring carry the knock-in X Chromosome and were mated with B6 males.

N2 offspring were analyzed for the presence of the KI allele by PCR.

Reporter Gene Detection. Adult male hemizygous Mini Promoter and age matched control mice were perfused with 4% paraformaldehyde (PFA) as previously described (Young, Berry et al. 2002). Whole brains and eyes were dissected out and post-perfusion immersion fixed with PFA for 2 hours at 4° C. The brains were sectioned using a coronal or sagittal brain mold (Electron Microscopy Sciences) at 1 mm and sections were placed in 12-well tissue culture plates. One whole eye and one half-cut eye, using a razorblade, was also placed in the plate. LacZ expression was detected by using 5-bromo-4-chloro-3-indolyl-β-D-galactopyranoside (X-Gal) as the substrate. The X-Gal staining solution contained the following: 1.0 mg/ml X-Gal, 2 mM potassium ferricyanide, 2 mM potassium ferrocyanide, and 40 mM MgCl2 in PBS. In brief, brain sections were rinsed with phosphate buffered saline (PBS), then incubated with X-Gal (Boeringer Mannheim, Indianapolis, Ind.) at 37° C., usually overnight. After staining the tissue was rinsed with PBS and moved into PBS containing 0.02% azide for storage. Eyes were further processed by post-fixing with 4% PFA for 2 hours at room temperature. After fixation, eyes were rinsed with PBS and cryoprotected in 25% sucrose-PBS at 4° C. overnight. Eyes were removed from the solution and blotted with a KimWipe before embedment in Optimal Cutting Temperature (OCT) alongside positive and negative controls. 12 µm sections were taken using a Microm HM 550 cryostat and directly mounted onto SuperFrost Plus microscope slides. Bright field images were taken on a Leica MZ125 dissecting microscope and photographed using an Olympus Coolsnap cf color camera with the ImagePro software package.

Example 1

Selection of PCP2 Mini-Promoter Elements

Figure 2:
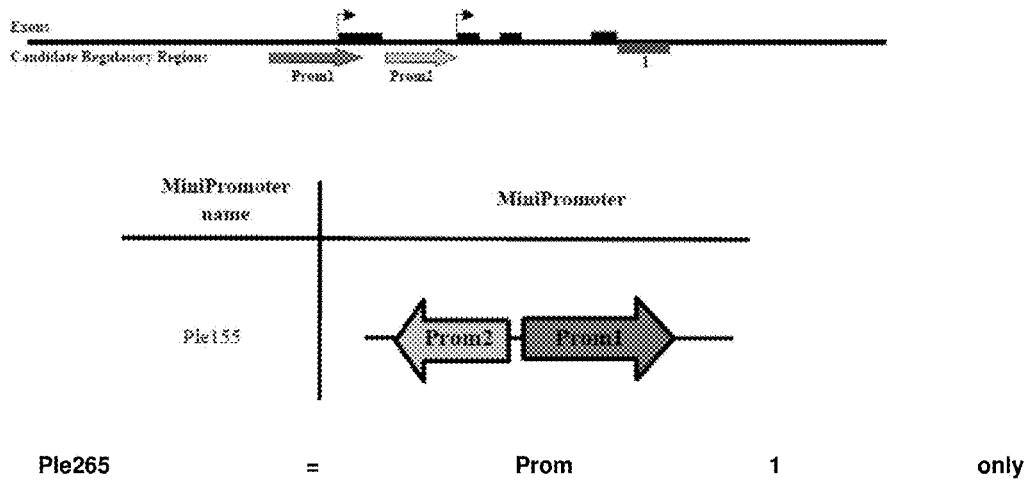
FIG. 2—PCP2 Mini-Promoter design. Prom1 corresponds to the basal promoter (SEQ ID NO: 2) while Prom2 corresponds to the regulatory element derived from intron 1 (SEQ ID NO: 3). The Prom 2 element in Ple155 is arranged upstream of the Prom 1 and is in reverse orientation from the natural genomic configuration.

Two regulatory regions of the human PCP2 promoter region were selected. The first (Prom1 in FIG. 2) represents the primary basal promoter for the gene. The second (Prom2) is located in intron 1 of the gene—this region was selected, however it was placed in a reverse orientation, to prevent unwanted transcription from this regulatory element, as it may also function as a weak promoter element in its forward orientation. The PCP2 basal promoter (SEQ ID NO: 2) and regulatory region (SEQ ID NO: 3) were chosen based on these criteria. Combination of the basal promoter (SEQ ID NO: 2) and regulatory region (SEQ ID NO: 3) in a non-native configuration created the PCP2 mini-promoter (SEQ ID NO: 1) used to create Ple155. The basal promoter alone created the PCP2 mini-promoter (SEQ ID NO: 2) used to create Ple265.

Example 2

Expression of Reporter in Neuronal Cells by Ple155 Promoter Element (PCP2 Mini-Promoter Comprising PCP2 Regulatory Element Combined in Non-Native Configuration with PCP2 Basal Promoter=SEQ ID NO: 1)

Figure 3:
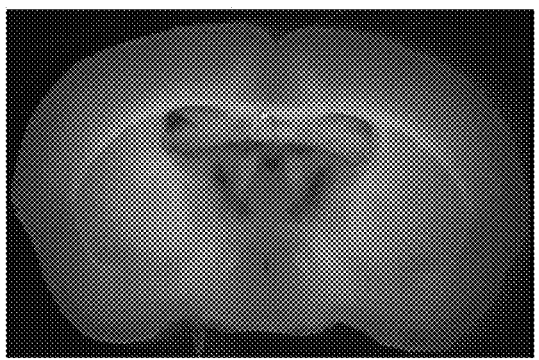
Figure 3:
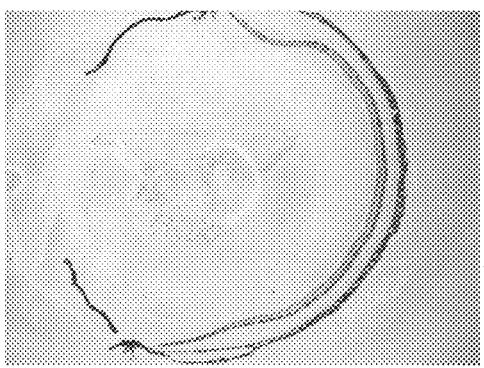
Figure 3:
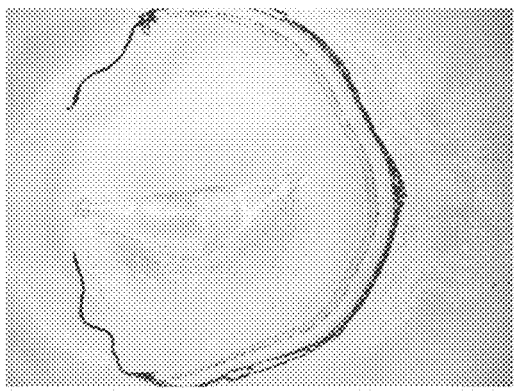
Figure 3:
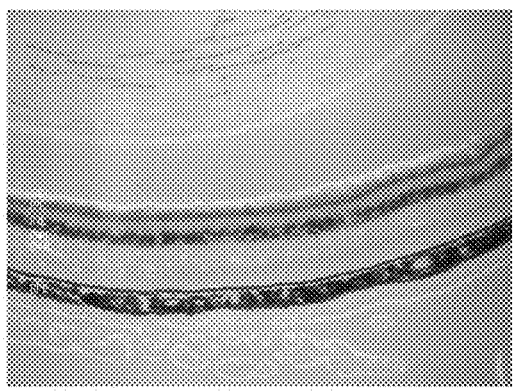

The PCP2 DNA expression vector comprising the PCP2 promoter element corresponding to SEQ ID NO: 1 (which is itself comprised of SEQ ID NO: 2 linked to SEQ ID NO: 3) was introduced into mouse embryonic stem cells (ESCs) at the HPRT locus. The ESCs were used to generate genetically modified mice containing PCP2. Immunohistochemical and immunofluorescence analysis of mouse brain tissue slices revealed lacZ reporter expression in a subpopulation of cells residing in the anterior thalamus of the brain (FIG. 3A). Analysis of eye tissue revealed expression in the inner nuclear layer of the retina. There are processes or additional staining observed in the inner plexiform layer. The expression pattern is consistent with the known expression of the PCP2 gene in bipolar cells (FIG. 3B-D).

Barski, J. J., K. Dethleffsen, et al. (2000). "Cre recombinase expression in cerebellar Purkinje cells." *Genesis* 28(3-4): 93-98.

Bronson, S. K., E. G. Plaehn, et al. (1996). "Single-copy transgenic mice with chosen-site integration." *Proc Natl Acad Sci U S A* 93(17): 9067-9072.

Cheng, J., A. Dutra, et al. (2004). "Improved generation of C57BL/6J mouse embryonic stem cells in a defined serum-free media." *Genesis* 39(2): 100-104.

Clapcote, S. J. and J. C. Roder (2005). "Simplex PCR assay for sex determination in mice." *Biotechniques* 38(5): 702, 704, 706.

Hanno, Y., M. Nakahira, et al. (2003). "Tracking mouse visual pathways with WGA transgene." *Eur J Neurosci* 18(10): 2910-2914.

Hogan, B., R. Beddington, et al. (1994). *Manipulating the mouse*. Cold Spring Harbor, Cold Spring Harbor Laboratory Press.

Jasin, M., M. E. Moynahan, et al. (1996). "Targeted transgenesis." *Proc Natl Acad Sci U S A* 93(17): 8804-8808.

Oberdick, J., R. J. Smeyne, et al. (1990). "A promoter that drives transgene expression in cerebellar Purkinje and retinal bipolar neurons." *Science* 248(4952): 223-226.

Ponchio, L., L. Duma, et al. (2000). "Mitomycin C as an alternative to irradiation to inhibit the feeder layer growth in long-term culture assays." *Cytotherapy* 2(4): 281-286.

Serinagaoglu, Y., R. Zhang, et al. (2007). "A promoter element with enhancer properties, and the orphan nuclear receptor RORalpha, are required for Purkinje cell-specific expression of a Gi/o modulator." *Mol Cell Neurosci* 34(3): 324-342.

Smeyne, R. J., T. Chu, et al. (1995). "Local control of granule cell generation by cerebellar Purkinje cells." *Mol Cell Neurosci* 6(3): 230-251.

Tomomura, M., D. S. Rice, et al. (2001). "Purification of Purkinje cells by fluorescence-activated cell sorting from transgenic mice that express green fluorescent protein." *Eur J Neurosci* 14(1): 57-63.

van der Weyden, L., D. J. Adams, et al. (2002). "Tools for targeted manipulation of the mouse genome." *Physiol Genomics* 11(3): 133-164.

Vandaele, S., D. T. Nordquist, et al. (1991). "Purkinje cell protein-2 regulatory regions and transgene expression in cerebellar compartments." *Genes Dev* 5(7): 1136-1148.

Yoshihara, Y., T. Mizuno, et al. (1999). "A genetic approach to visualization of multisynaptic neural pathways using plant lectin transgene." *Neuron* 22(1): 33-41.

Young, K. A., M. L. Berry, et al. (2002). "Fierce: a new mouse deletion of Nr2e1; violent behaviour and ocular abnormalities are background-dependent." *Behav Brain Res* 132 (2): 145-158.

Zhang, X. M., B. Y. Chen, et al. (2005). "Transgenic mice expressing Cre-recombinase specifically in retinal rod bipolar neurons." *Invest Ophthalmol Vis Sci* 46(10): 3515-3520.

What is claimed is:

1. An isolated polynucleotide comprising a PCP2 regulatory element with at least 95% sequence identity to SEQ ID NO: 3 in a reverse orientation, operably linked to a PCP2 basal promoter with at least 95% sequence identity to SEQ ID NO: 2, wherein the spacing between the PCP2 regulatory element and the PCP2 basal promoter is not more than 500 nucleotides.

2. The isolated polynucleotide of claim 1, operably linked to an expressible sequence.

3. A vector comprising the isolated polynucleotide of claim 1.

4. A cell comprising the vector of claim 3.

5. The cell of claim 4, wherein the vector is stably integrated into the genome of the cell.

6. The cell of claim 4, wherein the cell is a stem cell, neuronal cell, or a retinal cell.

7. A method of expressing a sequence of interest, the method comprising operably linking the sequence of interest to the polynucleotide of claim 1; and introducing the operably linked sequence of interest into a cell permissive for expression from the PCP2 mini-promoter.

8. The isolated polynucleotide of claim 1 wherein the spacing between the PCP2 regulatory element and the PCP2 basal promoter is not more than 100 nucleotides.

* * * * *

SEQUENCE LISTING

<160> NUMBER OF SEQ ID NOS: 3

<210> SEQ ID NO 1
<211> LENGTH: 1652

<212> TYPE: DNA
<213> ORGANISM: H. sapiens

<400> SEQUENCE: 1

| | | | | | |
|---|---|---|---|---|---|
| tcagcagatt | gaagaagccc | tcctggtctg | gggagcccgc | ctggggacag | actcgctcag | 60 |
| tctggttggc | ccttcagctt | gggggcccct | cccaaacttt | cctagccagc | ttgctcacac | 120 |
| cctgaccccg | gggcctgccg | tccccacttc | ctcagctctc | accatggtcc | ccgccgatcc | 180 |
| tctctgcaga | gctgttctga | atgagacatg | agtctcctttc | ccaatcccgg | ccccgcccc | 240 |
| aggggccctg | ccagcagtg | ccacttcacg | tggtaccgct | tcaagggaca | ggctccgatg | 300 |
| cgtgtcccgc | cgtcctagat | tggggcctga | tgagtgtggc | ctgggagctg | ggacacgaat | 360 |
| cagggaaaca | tggcccagga | gctacccca | ggtcccagca | tctcccatca | ataggggtcc | 420 |
| acacggagag | ccctgccctc | tgccctgggg | cctggcactc | agaccccaa | gcccaccagc | 480 |
| cccttttctac | agccacaact | gggtcagggg | gtcctaggag | actcactcgt | taattaggtg | 540 |
| ccctacaaac | taattagtct | tgtcaatcat | gggctctgag | accttgagct | ggggtgggg | 600 |
| tgggggcagg | gccctctcac | ctcggcacag | gggcctgagc | cttcctccgt | cttctcctcc | 660 |
| tgatccggac | acttcattgg | catagaggga | gagagtgtga | acttggccct | ttgtggaaca | 720 |
| gaggaggctc | gggcagaggt | ggtgatagtg | cagcccattc | attctgagat | gaaacttcca | 780 |
| ctggtttccg | taaagacgtc | ttggggaggg | aagggaaggg | gatggggacc | tcccagtggt | 840 |
| atccctgct | tgggcactga | gggaaagcca | cagtggctcg | ggtaaaagg | cagggacatc | 900 |
| ctctccccgc | ctgcctctgt | ccccaggag | tctcgcctcc | tgttcccacc | tggggctagg | 960 |
| gtgatagagg | agaggagata | gctcaacctg | gcatttaggt | ggtgtgggaa | caggagaccc | 1020 |
| cagactttct | tgtttggg | tctggggcag | gcaaccaggc | tccagggaca | gtgagttgaa | 1080 |
| ggaagggtgg | ctgggagacc | ccttgacttg | ctgccaagga | gacagagctg | gagctagggt | 1140 |
| ggcgggtggt | gtctgaggca | ggtgcagaga | gggagggagg | gaaggggcct | ttgactccaa | 1200 |
| cctccttttt | ctttaccgac | tgcaggtggc | agctgccctt | ccaggagcca | gtggggaac | 1260 |
| ctgggtggct | gggtggggac | acctgcaagt | cctcccctaag | ccagctacca | ccctacactg | 1320 |
| ttggcctccc | ttctccaact | gtggggacgc | tgctcaggcc | ttttgtgaca | tcacacctga | 1380 |
| gagtccctgg | ggtccagtca | ttgctgctgg | gcacagcgag | gtccaagctc | aggtcgccct | 1440 |
| gcccctacc | caccatgcca | gatccagcat | cgttgtgggc | aaacaattat | ctggatgatc | 1500 |
| tttatgggc | ttaagcttgg | gtgggagcag | atggggcatg | agctgggat | tggggatgg | 1560 |
| ggggaatcca | caccccacg | tcctggacgt | ttaaaaggcc | ctctctggca | ctgggccggg | 1620 |
| gcagaggcca | gcagaaaagt | gactggagtc | ca | | | 1652 |

<210> SEQ ID NO 2
<211> LENGTH: 986
<212> TYPE: DNA
<213> ORGANISM: H. sapiens

<400> SEQUENCE: 2

| | | | | | |
|---|---|---|---|---|---|
| ggacacttca | ttggcataga | gggagagagt | gtgaacttgg | ccctttgtgg | aacagaggag | 60 |
| gctcgggcag | aggtggtgat | agtgcagccc | attcattctg | agatgaaact | tccactggtt | 120 |
| tccgtaaaga | cgtcttgggg | agggaaggga | agggatggg | gacctcccag | tggtatcccc | 180 |
| tgcttgggca | ctgagggaaa | gccacagtgg | ctcggggtaa | aaggcaggga | catcctctcc | 240 |
| ccgcctgcct | ctgtccccag | ggagtctcgc | ctcctgttcc | cacctggggc | tagggtgata | 300 |

```
gaggagagga gatagctcaa cctggcattt aggtggtgtg ggaacaggag accccagact      360
ttcttgtttt ggggtctggg gcaggcaacc aggctccagg gacagtgagt tgaaggaagg      420
gtggctggga gacccttga cttgctgcca aggagacaga gctggagcta gggtggcggg      480
tggtgtctga ggcaggtgca gagagggagg gagggaaggg gcctttgact ccaacctcct      540
ttttctttac cgactgcagg tggcagctgc ccttccagga gccagtgggg gaacctgggt      600
ggctgggtgg ggacacctgc aagtcctccc taagccagct accacccatc actgttggcc      660
tcccttctcc aactgtgggg acgctgctca ggccttttgt gacatcacac ctgagagtcc      720
ctggggtcca gtcattgctg ctgggcacag cgaggtccaa gctcaggtcg ccctgccccc      780
tacccaccat gccagatcca gcatcgttgt gggcaaacaa ttatctggat gatctttatg      840
gggcttaagc ttgggtggga gcagatgggg catgagctgg ggatttgggg atgggggaa      900 tccacacccc cacgtcctgg acgtttaaaa ggccctctct ggcactgggc cggggcagag      960
gccagcagaa aagtgactgg agtcca                                           986

<210> SEQ ID NO 3
<211> LENGTH: 666
<212> TYPE: DNA
<213> ORGANISM: H. sapiens

<400> SEQUENCE: 3
tcagcagatt gaagaagccc tcctggtctg gggagcccgc ctggggacag actcgctcag       60
tctggttggc ccttcagctt gggggcccct ccccaaactt cctagccagc ttgctcacac      120
cctgaccccg gggcctgccg tccccacttc ctcagctctc accatggtcc ccgccgatcc      180
tctctgcaga gctgttctga atgagacatg agtctccttc ccaatccgg ccccgcccc       240 aggggccctg gccagcagtg ccacttcacg tggtaccgct tcaagggaca ggctccgatg      300
cgtgtcccgc cgtcctagat tggggcctga tgagtgtggc ctgggagctg ggacacgaat      360
cagggaaaca tggcccagga gctacccca ggtcccagca tctcccatca atagggtcc       420 acacggagag ccctgccctc tgccctgggg cctggcactc agaccccaa gcccaccagc      480 cccttctac agccacaact gggtcagggg gtcctaggag actcactcgt taattaggtg      540
ccctacaaac taattagtct tgtcaatcat gggctctgag accttgagct ggggtgggg      600 tgggggcagg gccctctcac ctcggcacag gggcctgagc cttcctccgt cttctcctcc      660
tgatcc                                                                 666
```